United States Patent
Shoham et al.

(10) Patent No.: US 12,035,979 B2
(45) Date of Patent: Jul. 16, 2024

(54) AUTONOMOUS ROBOT TRACKING

(71) Applicant: Mazor Robotics Ltd., Caesarea (IL)

(72) Inventors: Moshe Shoham, Hoshaya (IL); Yizhaq Shmayahu, Ramat HaSharon (IL)

(73) Assignee: Mazor Robotics Ltd., Caesarea (IL)

(*) Notice: Subject to any disclaimer, the term of this patent is extended or adjusted under 35 U.S.C. 154(b) by 243 days.

(21) Appl. No.: 17/536,312

(22) Filed: Nov. 29, 2021

(65) Prior Publication Data
US 2022/0168048 A1    Jun. 2, 2022

Related U.S. Application Data (60) Provisional application No. 63/119,358, filed on Nov. 30, 2020.

(51) Int. Cl.
*A61B 34/20*    (2016.01)
*A61B 17/16*    (2006.01)
(Continued)

(52) U.S. Cl.
CPC .......... *A61B 34/20* (2016.02); *A61B 17/1622* (2013.01); *A61B 17/1703* (2013.01);
(Continued)

(58) Field of Classification Search
CPC ..... A61B 34/20; A61B 34/30; A61B 17/1622; A61B 17/1703; A61B 2034/105;
(Continued)

(56) References Cited

U.S. PATENT DOCUMENTS 9,125,556 B2    9/2015  Zehavi et al.
2018/0235715 A1*    8/2018  Amiot .................. G01B 11/25
(Continued)

FOREIGN PATENT DOCUMENTS

WO    WO 2006/075331    7/2006
WO    WO 2019/036006    2/2019

OTHER PUBLICATIONS

International Search Report and Written Opinion for International (PCT) Patent Application No. PCT/IL2021/051425, dated Mar. 11, 2022, 13 pages.

*Primary Examiner* — Kevin T Truong
*Assistant Examiner* — Diana Jones
(74) *Attorney, Agent, or Firm* — Sheridan Ross P.C.

(57) ABSTRACT

A system for tracking the position of a surgical tool manipulated by a surgical robotic system, to determine that the tool is correctly positioned and orientated. Miniature 3-D tracking cameras are mounted on the end effector of the robotic system, one viewing markers on the surgical tool, and the other markers attached to the anatomy part being operated on. The initial spatial position and orientation of the surgical tool on the surface of the anatomy part is measured, and the progress of the surgical tool into the anatomic body part is tracked using one of the miniature cameras. The cameras or sensors are close to the surgical region of interest, and all the mechanical and sensor elements necessary for the system operation are mounted within the realm of the robot. The system thus avoids interruption of communication between a remotely positioned navigation camera and the robot or patient.

17 Claims, 5 Drawing Sheets

(51) Int. Cl.
  *A61B 17/17* (2006.01)
  *A61B 34/10* (2016.01)
  *A61B 34/30* (2016.01)
  *A61B 90/00* (2016.01)

(52) U.S. Cl.
  CPC ........ *A61B 34/30* (2016.02); *A61B 2034/105* (2016.02); *A61B 2034/2057* (2016.02); *A61B 2034/2065* (2016.02); *A61B 2090/367* (2016.02); *A61B 2090/371* (2016.02)

(58) Field of Classification Search
  CPC ...... A61B 2034/2057; A61B 2090/367; A61B 2090/371
  See application file for complete search history.

(56) References Cited

U.S. PATENT DOCUMENTS

| | | |
|---|---|---|
| 2019/0038362 A1 | 2/2019 | Nash et al. |
| 2019/0388161 A1* | 12/2019 | Cicchini ................ A61B 90/11 |
| 2020/0078097 A1* | 3/2020 | Gregerson ......... A61B 17/3423 |
| 2020/0107887 A1* | 4/2020 | Roessler ................ A61B 34/10 |
| 2020/0146754 A1 | 5/2020 | Row et al. |

* cited by examiner

AUTONOMOUS ROBOT TRACKING

CROSS REFERENCE TO RELATED APPLICATIONS

This application claims priority to U.S. Provisional Application No. 63/119,358, filed on Nov. 30, 2020, and entitled "Autonomous Robot Tracking", the entirety of which is hereby incorporated by reference.

FIELD

Embodiments of the present disclosure describe technology related to the field of robotic tracking of surgical tools, for example, as applied to orthopedic surgical treatments.

BACKGROUND

In some situations, the success of robotic assisted image-based surgery is dependent on accurate registration between pre-operative images of the region of interest and the intraoperative surgical field. Precision of registration can be of paramount importance in situations where the entire surgical process depends on accurately identifying anatomical features in the patient that correspond to those identified in the preoperative images, upon which the operation was planned. Once accurate registration has been established, the robotic surgical system can direct the end effector to accurately position a surgical tool to perform a surgical plan generated from the preoperative three-dimensional images. In many surgical plans, some of the procedures may involve manual manipulation on the part of the surgeon. One such exemplary instance is in the drilling of holes in orthopedic procedures, in which the surgeon manually performs the drilling procedure using a surgical drill. In order to determine the longitudinal position of the drill bit, namely the insertion depth of the drill bit into the subject's bone, a monitoring system must be used to track the position of the drill with the accuracy required to prevent over insertion of the drill, possibly with concomitant damage to the subject. In this respect, real-time monitoring is essential in order to maintain constant knowledge of the position of the drill.

Different systems, using a variety of equipment and alignment methods, have been developed to ensure accurate monitoring of the drill position during a surgical procedure. One method is to use a navigation system, in which the motion of the object to be tracked is achieved by viewing the surgical field with a three-dimensional camera system, which is capable of imaging three-dimensional markers attached to the object or objects whose position is to be tracked, and the anatomic feature on which the surgical procedure is being performed. By this means it becomes possible to track, for instance, the position and orientation of a surgical drill relative to the orthopedic element on which the drill is operating. These systems often rely on a clear field of view between the camera and the markers, where the line of sight between the camera needs to be unimpeded by objects such as the surgeon's arm or the robotic arm. Similar systems relying on other forms of imaging, such as electromagnetic radiation, ultrasound waves, or radio locating transmissions may also require similar conditions.

SUMMARY

The present disclosure describes, inter alia, new exemplary systems and methods for tracking the position of an object, such as a surgical tool, being manipulated by a surgical robotic system, such that it can be determined that the tool is in the correctly planned position and at the correctly planned orientation to perform the task assigned to it according to a predetermined surgical plan. These objectives are achieved by use of one or more miniature tracking cameras mounted on a part of the robotic system close to the surgical region of interest, such as on the end effector. These embodiments determine the initial spatial position and orientation of the tool on the surface of the anatomy body part on which it is to operate, and are also able to monitor the progress of the tool into the anatomic body part as it performs its function. An advantage of some of the systems described in this disclosure is that they do not require any cameras or sensors remote from the robot itself, and that all of the mechanical and sensor elements necessary for the system operation—but not necessarily the control system—can be mounted within the realm of the robot. As a result, these embodiments are less prone, or even immune to disruption of operation because of the interruption of communication between a remote camera or sensor and the robot or the patient.

Embodiments of the present disclosure achieve these objectives by incorporating one or more miniature three-dimensional sensor cameras most advantageously mounted on the actuating arm or end effector of the robot, this being the closest part of the robot to the tool and the region of the surgery, though other close locations could also be used. Hereinafter, the term end effector will be used generically to refer to this part of the robot. These miniature sensor cameras have fixed positions relative to the end effector. Each camera or sensor tracks an object's position and orientation relative to the end effector, by imaging a three-dimensional reference marker element or reference frame rigidly attached to the object being tracked, and analyzing the resulting three-dimensional images, to determine the position and orientation of the tracking marker, and hence of the object. For suitably equipped camera systems, this analysis may also be accomplished by using the camera's direct three-dimensional output information configurations. An initial correlation must be established between the three-dimensional spatial position and orientation of the object to be tracked, and the spatial position and orientation of the three-dimensional marker, which is what is tracked by the cameras. Tracking the position of remote objects relative to the end effector can provide several different advantages.

Firstly, tracking a remote object, such as the marker attached to a moveable surgical tool, or more usually, to the tool driver to which the tool itself is attached, enables the pose of the tool to be known relative to the end effector, and hence, relative to the robotic co-ordinate system. In order to overcome any confusion that may arise from differences in both the nomenclature used and in the specific tool configuration, between such surgical tool holders or drivers, and the tool which the holder rotates or vibrates or simply holds, the term "surgical tool" is used henceforth to denote the tool driver together with the surgical tool which it is holding, The tip of the bit which performs the procedure on the anatomical part of the subject's body, is then accordingly called the tip of the surgical tool. This nomenclature is used whether the tool holder is a drill, or a milling machine, or an ultrasonic tool holder, or even a tool holder whose operating tool does not move relative to the tool holder.

The angular orientation of the surgical tool is generally already known in the robotic co-ordinate system as well as two coordinates of the position, since the coordinates of the tool guide through which the surgical tool passes is known to the robot control system. However, the longitudinal position of the surgical tool relative to the tool guide, is not known to the robot system, at least in systems where the tool insertion is performed manually by the surgeon. The use of such a tracking camera on the end effector, directed towards the surgical tool marker element, thus enables a determination of the complete tool pose to be obtained, including the longitudinal position of the surgical tool. The longitudinal surgical tool position relative to the target on which it is to operate, can be determined by a preliminary calibration of the position of the surgical tool tip relative to the marker reference frame on the surgical tool. Alternatively, that position can be determined by touching the surgical tool tip onto the surface of the target on which it is to operate, in order to define a reference position relative to which the surgical tool motion will be referred.

Secondly, by using a three-dimensional tracking camera mounted on the end effector and directed towards the marker attached to a remote object, which in this application may be the anatomic body part on which the robotic system is to perform the surgical procedure, these embodiments can track the pose of the anatomic body part relative to the end effector, and hence, relative to the robotic co-ordinate system.

Thirdly, combination of the above two advantages provides direct co-ordinate relationship between the surgical tool and the anatomic body part on which the robotic system is to perform the surgical procedure, since both are referred to the same base co-ordinate system of the robot and its end effector. Consequently, once registration has been performed between intraoperative fluoroscope images of the anatomical body part, including the reference marker element, with preoperative images from the three-dimensional image set, such that the intraoperative pose of the body part can be related to the three dimensional higher resolution pre-operative images from which the surgical plan has been created, then intraoperative optical tracking of the marker element enables the position of the surgical tool to be related to the preoperative three dimensional high resolution images of the region of interest. This makes it possible to implant in real time, an image of the surgical tool tip, whose pose is known from the tool tracking camera output, onto a preoperative high-resolution image taken from the preoperative three-dimensional set of images. This implementation thus enables the surgeon to track the position of the tip of the surgical tool in real time, by means of an image of the tool tip region implanted on a three dimensional high resolution image, such as a CT or MM image, from which the surgical plan was developed. In U.S. Pat. No. 9,125,556, for "On-site Verification of Implant Positioning", commonly owned and having a common inventor with the present application, there is described a method by which a surgical insert, imaged by intraoperative X-ray fluoroscopy, can be implanted on three dimensional higher resolution preoperative images, this providing a major advantage over viewing the insert in an intraoperative X-ray image, which has much lower resolution. In the presently described implementation, such an image implantation using the image information generated by both the tool directed camera, and the body part directed camera, can provide a continuous, real-time view of a surgical tool implanted onto a three dimensional high resolution CT or MRI image of the region of interest.

Some of the presently described methods have a further clinical advantage over some of those of U.S. Pat. No. 9,125,556, in that not only is the three-dimensional position of the tool obtained as real-time tracking in a high resolution image, but also, that this is achieved using only an optical imaging camera, and does not involve, other than an initial calibrating X-ray image or images, the use of continuously repeated X-ray images whenever the tool position is to be positively determined relative to the subject's anatomy.

All of these above aspects can be used in different implementations of the systems and methods as will be fully described in this disclosure.

Another advantage of embodiments described herein is that the short distances between the cameras and the anatomical reference frame and the surgical reference frame not only eliminate the main problem of line-of-sight obstruction but also allows for much higher accuracy, since the cameras can typically be less than a meter, and even as close as 20 cm away from the reference frames rather than 3 meters, which is a typical distance away of a remote navigation system camera array.

One more application of this approach is registration by touching anatomical landmarks. The end-effector attached camera follows the hand-held tool as it touches known anatomical landmarks, thus obtaining registration. According to a further embodiment, a laser pointer could be used for implementing such anatomic position location. The laser pointer is directed by the surgeon at a predetermined anatomic feature, and the camera can detect the impingement of the laser beam on the anatomical feature using an imaging processing routine, most conveniently running on the controller. Since the pose of the imaging camera is known relative to the end effector of the robot, the detected position of the laser spot is thus known in the robotic co-ordinate system. Repetition of this ranging procedure a number of times, enables the entire region of the anatomical feature to be mapped in the co-ordinate system of the robot, without the need for image registrations.

According to yet another implementation, embodiments of the present disclosure are additionally used to verify the determination of the position of the surgical robot relative to the real-life intraoperative position of the anatomic body part. This is performed by using a camera directed to image a reference frame mounted in a fixed and rigid position relative to the body part, and thereby determining the position and orientation of the body part itself relative to the robotic end effector. Since that position and orientation has already been determined in the preliminary registration procedure, this second implementation can be used as a verification procedure to confirm the previously obtained position and orientation of the body part in the robot coordinate frame of reference.

The end effector is usually the most convenient and the most useful position on which to mount the imaging camera or cameras, since it is generally the closest position to the surgical tool and the body part, and such a mounting position is used throughout this description. However, it is understood that other positions on the robot could be used to mount the camera or cameras, so long as such a position provides close visual access to the imaged reference frames, in order to utilize the advantage of this system over previously described remote navigation or tracking system cameras, and the claimed systems and methods of the present disclosure, are intended to cover other such close mounting configurations.

Although the above described implementations of the autonomous tracking system have been applied to determining the pose of a robotically directed surgical tool and its anatomical target, further implementations can provide significant advantages also to hand-held and hand manipulated surgical tools. In these implementations, a surgical tool held and manipulated by a surgeon or by other medical personnel, can be equipped with a three-dimensional reference marker element or reference frame. The marker can be imaged by a three-dimensional tracking camera mounted on a robotic arm, which, unlike the remote cameras on previously used navigation systems, can be moved into close proximity of the surgical region and the manually maneuvered tool. Such an implementation enables the fulfilment of the two objectives mentioned hereinabove, namely (i) a significant increase in the positional accuracy obtained because of the closeness of the camera to the marker assembly, and (ii) good immunity from inadvertent obstruction of the line of sight between the camera and the marker it is tracking, also for manually performed surgical procedures. Since in this implementation, the position of the robotic arm is not limited by the need to position the surgical tool relative to the surgical site, the arm carrying the tracking camera can be moved without such limitations, as close as is required to the operating site, therefore increasing the accuracy of the positioning accuracy of the manually manipulated surgical tool. In this implementation, the system controller can make use of the positional awareness of the robotic arm, and hence of the tracking camera, in order to relate the position of the manually held surgical tool to the anatomic part on which it is operating, using the initially performed registration procedure between the robotic co-ordinate system and the surgical plan, as determined from the preoperative three-dimensional images of the surgical region of interest.

As a further embodiment of this method of tracking manual tool use, instead of using a single three-dimensional tracking camera on a robotic arm, two conventional two-dimensional cameras can be used, each on a separate robotic arm, and the cameras moved by separate motion of the two arms into the optimal positions for viewing the surgical site and determining the position of the marker elements by triangulation calculations. This embodiment has the advantage that the depth perception can be improved by selecting a larger separation distance of the cameras.

In any of the above described manually manipulated tool applications, since the co-ordinate system of the robotic system carrying the tracking camera or cameras is initially registered to images of the region of interest, and to the anatomy part on which the surgeon is operating, the internal arm positional awareness of the robotic system can compensate for changes in the positioning of the camera-carrying robotic arm, which have occurred since the initial known registration. In an alternative method of utilizing this embodiment, the tracking camera mounted on the robotic arm can also be aligned to track the pose of the anatomical part on which the surgeon is performing the procedure, using a marker frame attached to that anatomical part. In such a situation, the camera can directly relate the pose of the hand-held surgical tool to the pose of the anatomic part, without direct use of information of the initial registration.

In any of the above described implementations, the robotic controller can be configured to run routines for calculating the optimum position of the robotic arm or arms, using algorithms which determine the relationship between the available space around the operating region of interest, and the access of the tool, whether robotic or manually held. In the latter case, the system can also provide information to the surgeon about the best access position to the surgical site.

There is thus provided in accordance with an exemplary implementation of the devices described in this disclosure, a robotic tracking system comprising:
(i) a first tracking camera fixedly attached to a part of a robot, in a position that enables the first tracking camera to capture images of a first three-dimensional reference frame attached to a surgical tool;
(ii) a second tracking camera fixedly attached to a part of the robot, in a position that enables the second tracking camera to capture images of a second three-dimensional reference frame attached to an anatomical part of a subject; and
(iii) a control system adapted to determine at least a position of the surgical tool in the robot co-ordinate system, based on images of the first three-dimensional reference frame from the first tracking camera, and to determine the pose of the anatomical part of the subject in the robotic co-ordinate system, based on images of the second three-dimensional reference frame from the second tracking camera.

A further exemplary implementation of the robotic tracking systems of the present disclosure comprises:
(i) an imaging camera attached at a fixed location to a part of a robot, the field of view of the imaging camera being adjustable such that it can image:
  (a) a first three-dimensional reference frame attached to a surgical tool, and
  (b) a second three-dimensional reference frame attached to an anatomical part of a subject; and
(ii) a control system adapted to determine at least a position of the surgical tool in the robot co-ordinate system, based on camera images generated from the field of view including the first three-dimensional reference frame, and to determine the pose of the anatomical part of the subject in the robot co-ordinate system, based on camera images generated from the field of view including the second three-dimensional reference frame.

A yet additional embodiment of the robotic tracking systems described in this application comprises:
(i) an imaging camera fixedly attached to a part of a robot, the field of view of the imaging camera being such that it can image a first three-dimensional reference frame attached to a surgical tool; and
(ii) a control system adapted to:
  (a) determine at least a position of the surgical tool in the robot co-ordinate system, based on images of the first three-dimensional reference frame from the imaging camera, and
  (b) correlate the position of the tool with an anatomical part of the subject on which the tool is intended to operate, the pose of the anatomical part being determined from a navigational tracking system disposed in a fixed position in the vicinity of the robot, by use of a second three-dimensional reference frame attached to the anatomical part of the subject.

The robotic tracking system may enable the camera to recognize and follow anatomical landmarks without a need for a three-dimensional reference frame.

Furthermore, according to an additional example of the implementations shown in this disclosure, there is provided a robotic tracking system comprising:
(i) at least one imaging camera fixedly attached to a part of a robot, the field of view of the at least one imaging camera being such that it is adapted to image:
  (a) a first three-dimensional reference frame attached to a surgical tool and
  (b) a second three-dimensional reference frame attached to a part of an imaging system capable of imaging an anatomical body part of a subject; and
(ii) a control system adapted to:
  (a) determine at least a position of the surgical tool in the robot co-ordinate system, based on images of the first three-dimensional reference frame from the at least one imaging camera;

(b) determine the pose of the imaging system in the robot co-ordinate system, based on images of the second three-dimensional reference frame from the at least one imaging camera; and (c) correlate at least the position of the tool with the anatomical part of the subject on which the tool is intended to operate.

The systems described herein could include another exemplary robotic tracking system, comprising:

(i) a first imaging camera fixed to a part of a robotic system, such that its field of view includes a first three-dimensional reference frame attached to a surgical tool;

(ii) a second imaging camera fixed to the part of the robotic system, such that its field of view includes a second three-dimensional reference frame attached to an anatomical part of a subject on which a surgical tool is intended to operate, and (iii) a control system adapted to:

(a) correlate information regarding the pose of the surgical tool obtained by analysis of images of the first reference frame, with information regarding the pose of the anatomical part of the subject obtained by analysis of images of the second reference frame, and (b) use information regarding the spatial relation of the surgical tool tip to the surgical tool or to a point of contact of the tip with the surface of the anatomical part, so that the position of the surgical tool tip relative to the anatomical part of the subject, can be tracked by the controller.

Finally, there is further disclosed another embodiment of a robotic tracking system comprising:

(i) a first imaging camera (e.g., two-dimensional camera and/or three-dimensional camera) fixedly attached to a first robotic arm, and directed to generate first two-dimensional images of a three-dimensional reference frame attached to a hand-held surgical tool;

(ii) a second two-dimensional imaging camera fixedly attached to a second robot arm and directed to generate second two-dimensional images of the three-dimensional reference frame attached to the hand-held surgical tool; and (iii) a control system adapted to determine from a first two-dimensional image from the first camera, and from a second two-dimensional image from the second camera, the three-dimensional pose of the surgical tool in the coordinate system of at least one of the first and the second robots, wherein the positions of the first and second robotic arms are adapted to be held at a distance apart that provides the desired accuracy of the determined pose of the hand-held surgical tool.

One exemplary method of tracking a surgical tool manipulated by a robot, comprises:

(i) generating at least one image of a first three-dimensional referencing frame fixedly mounted to a surgical tool, the first referencing frame being disposed within the field of view of a first camera mounted on an end effector of a robot;

(ii) generating at least one image of a second three-dimensional referencing frame fixedly attached to an anatomical body part of a subject, the second referencing frame being disposed within the field of view of a second camera mounted on the end effector of the robot;

(iii) performing image analysis on at least one image generated by the first camera to determine the pose of the surgical tool relative to the end effector of the robot;

(iv) performing image analysis on at least one image generated by the second camera to determine the pose of the anatomical body part relative to the end effector of the robot; and (v) correlating the determined pose of the surgical tool with the determined pose of the anatomical body part so that the surgical tool can be tracked relative to the anatomical body part while executing a surgical procedure.

BRIEF DESCRIPTION OF THE DRAWINGS

The present invention will be understood and appreciated more fully from the following detailed description, taken in conjunction with the drawings in which:

FIG. 1A illustrates a system incorporating two imaging cameras, each aligned to its associated imaging location, FIG. 1B shows a similar system but with only one imaging camera, rotatable between the two different imaging locations, FIG. 1C shows a system in which an imaging camera is directed to view a C-arm used to image the surgical region and the robotic end effector, while FIG. 1D shows a manually held surgical tool with a tracking camera mounted on a robotic arm tracking its motion; and FIGS. 2A and 2B are schematic drawings of images derived from high resolution, three-dimensional image sets of a vertebra, obtained preoperatively, showing a surgical tool in its real time intraoperative position, implanted onto the preoperative image; FIG. 2A shows a lateral view, while

DETAILED DESCRIPTION

In order to determine the position and orientation of the remote object, a reference frame having a known three-dimensional arrangement of marker elements is attached rigidly to the remote object, and the camera is directed at that remote object to generate an image of the reference frame. Using the knowledge of the three-dimensional structure of the reference frame, the position and orientation of the reference frame relative to the camera can be determined by analysis of that image. Since the reference frame is rigidly attached to the remote object, this analysis enables the establishment of the position and orientation of the remote object relative to the camera, and hence also relative to the end effector.

The robotic system, in some embodiments, can operate in different modes, depending on the level of use made with registration techniques performed in robotic surgical procedures, to define the location of the robotic system relative to the position of the anatomic body part on which the surgical plan is to be implemented. According to a first implementation, the position of the robot base, or the co-ordinate frame of reference of the robot, and hence the position and angular orientation (jointly known as the pose) of the end effector, is known relative to the anatomical body part on which the surgical procedure is to be performed. This is achieved by determining the intraoperative position of the robot relative to the anatomical body part, for example, by use of intraoperative fluoroscope imaging that shows both the body part and, either a part of the robot base itself, or, for a remotely mounted robot, a part of an element such as a target held by the robotic end effector, that can define the position of the robotic end effector, and hence the robotic co-ordinate frame. The intraoperative fluoroscope images are used in conjunction with image registration between the intraoperative images showing the body part, and preoperative three-dimensional image sets of the same region of the subject, which also show the anatomical body part on which a surgical plan is executed. Once that procedure has been performed, the system then knows the pose of the surgical tool, since the surgical tool bit is held, generally within a tool guide, in a known position relative to the end effector and relative to the position of the body part on which the surgical tool is to perform its intended task.

However, if the surgical tool is to be moved longitudinally relative to the guide tube held by the end effector, the registration procedure described above is unable to determine that longitudinal position, and accurate knowledge thereof can be critical in order to ensure that the tool is not inserted too far into the body part, thereby possibly causing damage to the subject. Embodiments of the present disclosure provide the longitudinal position by analyzing the images of a reference frame attached to the surgical tool, such that the longitudinal position of the surgical tool is directly known relative to the end effector, without the need of remotely located scanning and navigation devices. In order for the position of the surgical tool tip to be known relative to the scanned position of the surgical tool itself, it is then necessary to perform a calibration procedure relating the position of the tool bit tip part of the surgical tool, to the position of the surgical tool body itself. Alternatively, the surgical tool bit part and its surgical tool body should have some correlating feature, such as by ensuring that the tool bit part is always locked into the surgical tool body part at a predetermined depth, such as by use of a mechanical registration stop, a visual insertion marker, or a similar arrangement. The tool bit part is then registered on insertion into the surgical tool driver part of the complete surgical tool, such that it always protrudes by a known measure from the surgical tool body part.

Figure 1A:
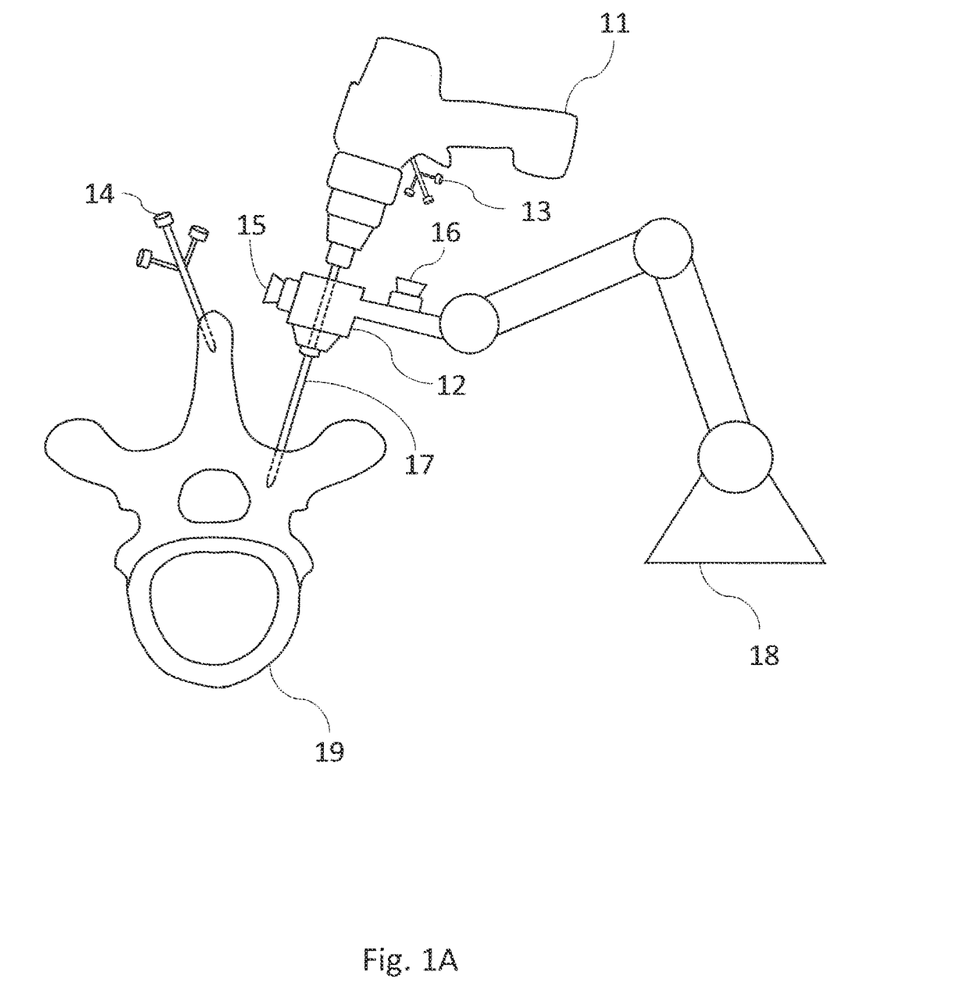
FIG. 1A, FIG. 1B, FIG. 1C and FIG. 1D illustrate schematically a robotic end effector incorporating elements for implementing the autonomous robotic tracking systems, according to different embodiments of the present application.

Reference is now made to FIG. 1A, which illustrates schematically a robotic end effector 12, incorporating elements for implementing an exemplary autonomous robotic tracking system of the present disclosure. The robotic end effector 12 is shown guiding a surgical tool 11, or more accurately, the operating part 17 of the surgical tool, such as a drill bit, through a guide sleeve into an anatomic part 19 of the subject, this being a vertebra of the subject's spine in the example shown, though it is to be understood that this is merely one example of the way in which the current system may be used and is not intended to limit the application. In order to implement the system, at least one three-dimensional registration frame, also known as a reference frame 14, is attached to the vertebra, and at least one three-dimensional registration frame 13, is attached to the surgical tool that the robotic end effector 12 is guiding into the vertebra of the subject, either robotically or with the surgeon's hand motion to manually insert the tool 11. Each of these three-dimensional registration frames 13,14, contains at least three marker elements arranged in a predetermined three-dimensional spatial layout such that a three-dimensional camera enables determination of the position and orientation of the registration frame by identifying the position and orientation of the marker elements. The position and orientation of the registration frame is used to define the pose of an object to which the registration frame is rigidly attached, be it the surgical tool or the anatomic part. In general, the larger the number of market elements used in the registration frame, the higher the accuracy of the proposed pose determination.

According to the implementation shown in FIG. 1A, the robot end effector 12 incorporates, two miniature cameras 15,16, rigidly fixed to the end effector. In some embodiments, these cameras are configured to capture three-dimensional images, from which, the pose of the registration frame being imaged can be determined from a knowledge of the spatial arrangement of the marker elements in the registration frame. In some embodiments the cameras are able to detect patterns on the marker elements on the registration frames (e.g., the marker elements on the three-dimensional registration frame 13). In some embodiments, the cameras can capture three-dimensional shapes, enabling the system to track known shapes without the use of marker elements. Such shapes could have known three-dimensional geometrical forms, such that their pose can be determined by any imaging process. One such example has been shown in International Patent application WO 2006/075331 for "Image Guided Robotic System for Keyhole Neurosurgery", commonly assigned to the present applicant, and having a common inventor, where a registration jig in the form of a wide-angled tetrahedron is shown. It is constructed so that all four planes can be seen from a wide range of scanning viewpoints, with sufficient area for adequate scan sampling. To facilitate plane identification, the angles between all adjacent tetrahedron faces should be different.

The first camera 16 is directed towards the registration frame 13 on the surgical tool 11, such that analysis of an image generated by that camera enables determination of the pose of the tool relative to the camera, and hence relative to the end effector 12 and thus, to the coordinate frame of the robot. Similarly, the second camera 15 is directed towards the registration frame 14 attached to the anatomy part 19 of the subject on which the surgical tool is to operate, such that analysis of the image by that camera, of the anatomy part registration frame 14 enables determination of the pose of the anatomy part relative to the camera, and hence also relative to the end effector 12 and thus to the coordinate frame of the robot. This assumes that the pose of the registration frame 14 relative to the pose of the anatomical body part 19 is known, such as by a previous imaging calibration procedure.

The cameras are mounted on the end effector in mutually fixed positions. Consequently, according to one exemplary method of this disclosure, comparison of the analyses of the images generated by the two cameras, enables the position and orientation of the surgical tool relative to the anatomic body part to be determined, without the need for any external or remote tracking system. This comparison may be performed by a control system which performs image processing on the images obtained from the two cameras. This control system can be either a separate module, or can constitute a part of the robotic control system itself, as shown in FIG. 1A, where the control system is shown conveniently housed in the base 18 of the robot, to which simple cable access is available for the image signals from the cameras, and for directing the robot control instructions to and from the various robotically controlled joints.

Figure 1B:
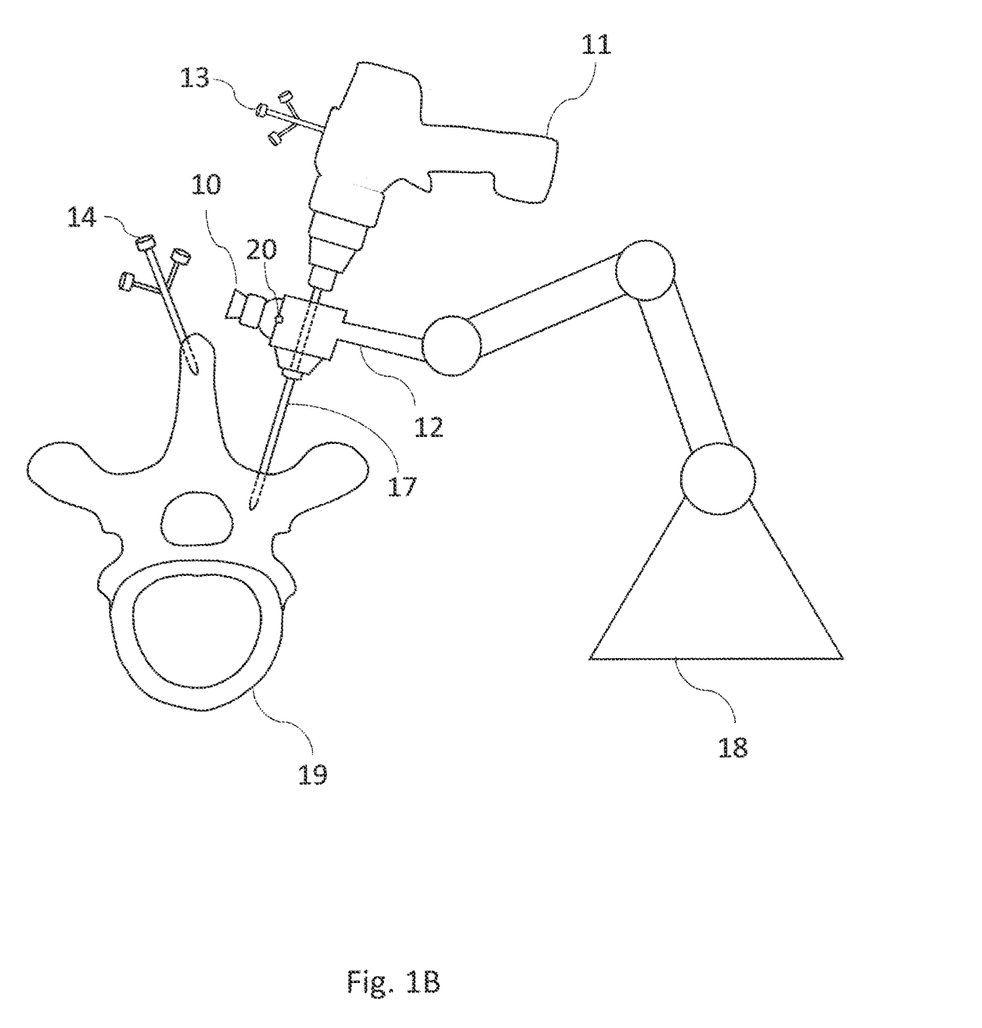

Reference is now made to FIG. 1B, which illustrates schematically an alternative implementation of the presently described systems, in which use is made of only a single imaging camera 10. This camera may be mounted on a pivot 20 on the end effector, and robotically controlled, either to adopt predefined orientations, or to switch between two preset orientations, such as by the use of mechanical stops so that a position-controlled robotic rotary motion mechanism is not necessary. The camera 10, can be directed either to image the reference frame marker 16 attached to and representing the position of the surgical tool 11, or directed to image the reference frame marker 14, attached to and representing the pose of the anatomy part 19 of the subject. In all other respects, the operation of the system of FIG. 1B is similar to that of FIG. 1A.

In use, a number of different procedures can be adopted to use the registration abilities afforded by embodiments of the present disclosure. In the first place, for all surgical procedures, a registration procedure relating the robot to the target bone can be performed, independently of whatever system is used to track the positions of the elements. This robot-to-bone registration can be achieved by any of various registration methods, such as, for example, the use of fiducial markers, often percutaneously mounted on the subject, which are then very clearly imaged in the preoperative three-dimensional image set, typically a CT or MRI image set. The exemplary fiducial markers can then be related to the robot position intraoperatively, either by a physical connection thereto of a reference plane of the robot, such as the base, or by intraoperative imaging which includes both the fiducial markers and an indication of the position of the robot base or the pose of a target held by the end effector, or by use of a touch probe whose position may be tracked by a navigation system, thus providing digitized location information of the fiducial points, and of the robot. Alternative registration methods may be based on comparison of the shape, outline or intensity of anatomical features as viewed in the three-dimensional preoperative image set, with the same features as appearing in fluoroscope images obtained intraoperatively. Matching all the features enables the position of the robot, as observed in the intraoperative fluoroscope images, to be registered to the anatomy of the subject as imaged preoperatively, and on the basis of which the surgical plan has been generated.

Once the registration of the robotic co-ordinate system to the co-ordinate system of the preoperative imaging set has been accomplished, the robotic end effector can then be programmed to perform the motions required in execution of the surgical plan, which is based on the preoperative images. For instance, in the case of a robotic alignment for the drilling of a hole for the insertion of a pedicle screw, the robot can direct the pose of the drill guide such that it is aimed at the insertion point both spatially and in orientation angle. However, the insertion depth of the drill part of the surgical tool can be more problematic to determine since the surgical tool is often inserted manually by the surgeon holding the surgical tool handle. Therefore, even though the robotic system has aligned the surgical tool for accurate entry position and path orientation, the insertion depth also needs to be accurately controlled in order to ensure that no damage ensues from excess insertion. Even if the drill travel is controlled by a separate motorized actuator, the origin position must be accurately determined, and the insertion depth monitored in order to ensure conformity of the controlled insertion.

In some previous systems, this has often been achieved by use of a navigation system located remotely from the region of the surgical operation, incorporating a tracking camera typically mounted above the surgical scene, and tracking the position of a marker mounted on the surgical tool. Such a navigation system can be blocked by the insertion of the surgeon's arm or another part of the body of one of the operating room staff, into the line of sight between the tracking camera and the markers on the surgical tool being tracked. In addition, such systems may generally be costly.

Embodiments of the present disclosure use the end effector tool camera, which can provide continuous real-time images of the tool registration frame to the control system module. This module analyzes the images and provides therefrom an accurate measurement of the longitudinal position of the surgical tool relative to the camera, and since the camera is rigidly mounted on the end effector, the surgical tool position is known in the robotic coordinate system. Since, from the initial robotic position registration, the pose of the end effector is known relative to the bone on which the surgical tool is operating, the pose of the surgical tool is also known relative to the bone into which the surgical tool is being inserted. However, in order to be able to track the insertion depth of the surgical tool into the bone on which the surgical tool is operating, it is necessary to relate the position of the surgical tool to the tracked position of the tool drill. This can be performed, for instance, by a calibration measurement of the position of the surgical tool tip relative to the reference frame. Alternatively, the operating procedure may also include the step of using the tool camera 16 to measure and define a base reference position of the surgical tool tip, in a position with the surgical tool tip just touching the surface of the anatomy part 19, such that the depth of insertion into the anatomic part 19, can be measured from that point in real time using the camera tracking procedure.

In an additional mode of operation, embodiments of the present disclosure may be used for verifying the accuracy of the intended positioning and insertion of the surgical tool, as determined by the preliminary registration of the robotic co-ordinate system with the preoperative image set on which the surgical plan was based, by using the second camera mounted on the end effector, and viewing the reference frame mounted in a fixed position relative to the bone on which the surgical procedure is being performed. Although the previously described method using the surgical tool directed camera, should, together with the robot registration, provide an accurate pose measurement of the surgical tool and its insertion depth, a verifying measurement can be performed in surgical procedures in order to ensure that an unexpected error in the previously described primary referencing method, does not result in bodily damage to the patient. The camera directed to the reference frame on the anatomy part, represents a measurement system, independent of any previous registrations, enabling the system to ascertain the position and orientation relative to the robotic co-ordinate system, of the body part on which the operation is being performed. The main measurement method involved image registration performed of the actual intraoperative position of the body part being operated on, with the robotic coordinate system, by one of the registration methods described hereinabove.

In situations in which the intraoperative imaging method is of sufficiently good resolution, this implementation therefore provides a method of relating the surgical tool pose and the tool tip position to the anatomical body part on which the tool is to perform the surgical process, without the need for preoperative imaging. The controller uses the commonly defined base—the end effector—to directly relate the positions of the surgical tool tip and of the bone structure to that common base. So long as the reference frame can be accurately related to the bone shape and structure of the anatomical part, the system according to this implementation looks simultaneously straight at the tool tip and at the anatomical body part, and can measure both of their positions, and hence their mutual positions, without any other preoperative registration.

In yet another mode of operation, a system implementation using only a single camera directed at the surgical tool reference frame is proposed. Since the position and orientation of the body part on which the procedure is to be performed may be known to the robotic system controller by an image registration procedure, and since the surgical tool pose may also be known from the robotic end effector pose as determined either from a full image registration procedure, or from a separate optical tracking measurement of the robot end effector pose, the only unknown information for carrying out the surgical procedure is the longitudinal position of the surgical tool. Therefore, according to this additional method, the system only needs a single robot-mounted camera directed in the direction of the surgical tool in order to ascertain the longitudinal position of the surgical tool, since its initial pose relative to the body part, is determined by the image registration procedure, or a separate optical tracking measurement of the robotic pose. This method and system is feasible since the robot pose can be determined by a remote tracking system more readily without fear of obstruction, than can the surgical tool position, for which a closely disposed scanning camera is an advantage.

Figure 1C:
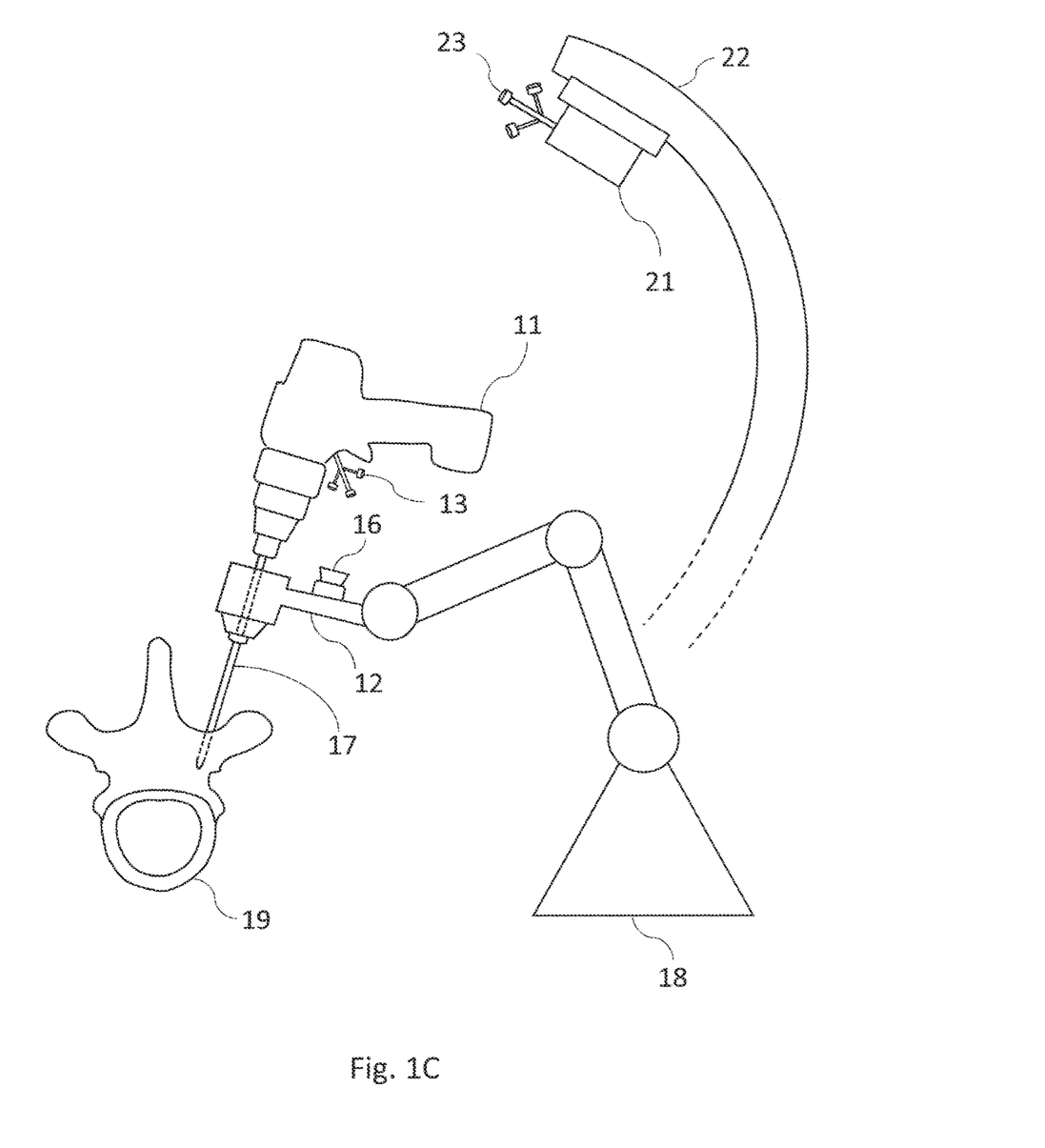

Reference is now made to FIG. 1C, which illustrates schematically a further implementation of the use of closely mounted scanner cameras. This implementation enables what could be termed a semi-automatic registration procedure, which renders the registration frame on the anatomic body part as superfluous, thus simplifying the entire procedure. According to this implementation, a registration frame 23 is mounted on the source 21 of the C-arm 22, or on any other convenient part of the C-arm in the region of the source, such that a scanning camera 16 mounted on the robotic end effector can image the C-arm source, and can thus determine its pose relative to the end effector. As an alternative to a dedicated registration frame, the system can use any alternative spatially defining feature on the C-arm, which when observed with a 3-dimensional scanning camera on the end-effector, can enable information regarding the pose of the C-arm to be obtained. The camera used can be the same camera 16 as that directed at the surgical tool, or a separate camera.

The co-ordinate system of the C-arm is thus known in the reference co-ordinate system of the robot. Additionally, since the C-arm imaging system now generates a set of images of the anatomical part of the subject, the features of that anatomical part are therefore known in the C-arm co-ordinate system, and consequently, also in the robotic co-ordinate system. There is thus achieved, a registration of the anatomical body part, and hence its pose, relative to the robotic end effector, without the need to attach a registration frame to the anatomic part, and without a camera to image that registration frame. This should increase positional accuracy, since a registration element attached to, or part of a C-arm component, will generally have a more definable placement than a registration frame attached to a body part on the end of a long K-wire. Once the registration of the body part to the robotic end effector is known, the various implementations of the system regarding the surgical tool pose relative to the body part can be performed, as previously described in this disclosure.

Figure 1D:
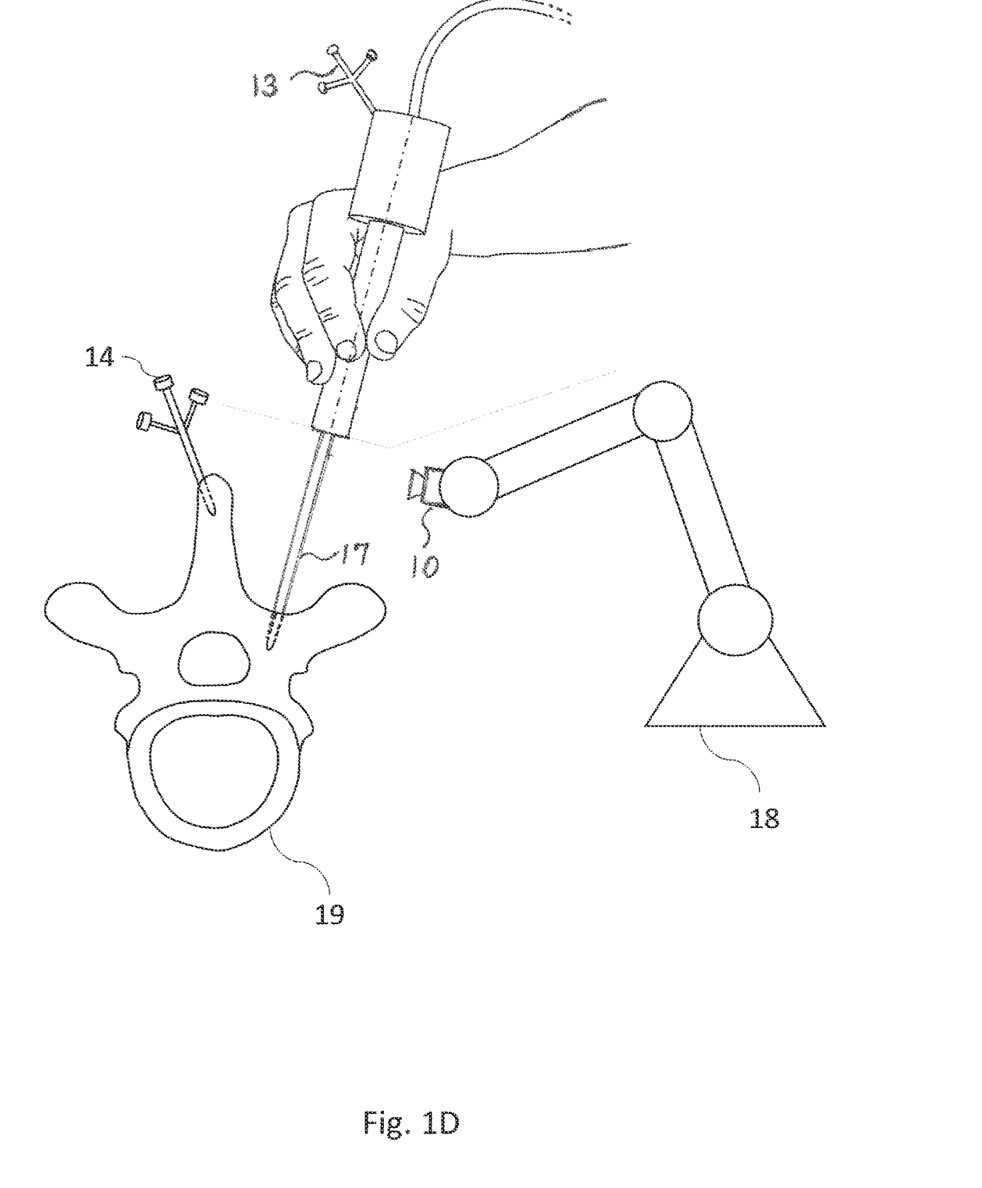

Finally, reference is made to FIG. 1D, which illustrates schematically one exemplary implementation of the use of a tracking camera 10 mounted on a robotic arm, to track the position of a hand manipulated surgical tool 17 as it is guided manually by the surgeon to perform a procedure on an anatomical part 19 of a subject. The pose of the hand-held surgical tool is determined by means of a three-dimensional tracking frame 13 mounted on the tool, and tracked by a camera 10 mounted on the robotic end effector of a surgical robot 18. In the exemplary system shown in FIG. 1D, the tracking camera is shown as a rotatable camera, such that it can track both the surgical tool 17, and a reference frame 14 attached to the vertebra 19 on which the surgeon is operating. However, it is to be understood that different arrangements may also be used, with the proviso that at least the pose of the hand-held surgical tool 17 is tracked by a tracking camera 10, which, by means of it being attached in a known manner to the end effector, has a pose which is known in the co-ordinate frame of the robotic system, such that it is also referenced to the position of the anatomic part 19 of the subject. According to one of these alternative embodiments (not shown in these drawings), instead of a single three-dimensional tracking camera as shown in FIG. 1D, two conventional cameras can be used, each on its own robotic arm, such that by positioning the two cameras somewhat distant from each other, meaning a greater distance apart than the double cameras installed in a three-dimensional tracking camera 10, a greater depth perception, and hence surgical accuracy, can be obtained.

Figure 2A:
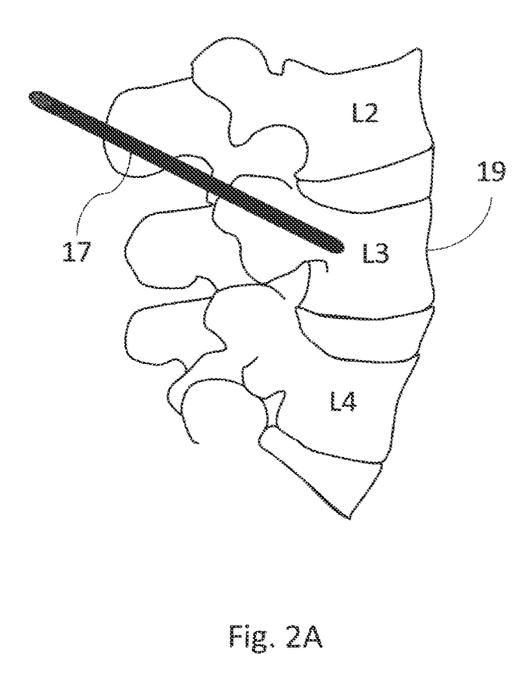
Figure 2B:
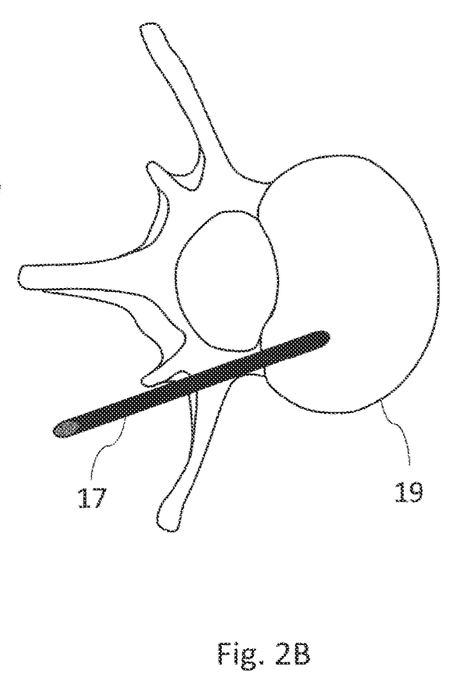
FIG. 2B shows an axial view.

Reference is now made to FIGS. 2A and 2B which show illustrations of an implementation showing further advantages of the present system, with schematic images derived from preoperatively generated high resolution, three-dimensional image sets of a vertebra 19, showing a surgical tool 11 in its real time intraoperative position, implanted onto the preoperative images. FIG. 2A shows a lateral view, while FIG. 2B shows an axial view. Such views can be obtained by a further implementation of the presently described tracking system, which provides direct co-ordinate relationship between the surgical tool and the anatomic body part on which the robotic system is to perform the surgical procedure, since both are referred to the same co-ordinate system of the robot and its end effector. Consequently, once registration has been performed between intraoperative fluoroscope images of the anatomical body part, with preoperative images from the three-dimensional image set, such that the intraoperative pose of the body part can be related to the higher resolution pre-operative images from which the surgical plan has been created, then intraoperative optical tracking of the marker element enables the position of the surgical tool to be related to the preoperative high resolution images of the region of interest. This then makes it possible to implant an image of the tool tip region in real time, known from the surgical tool tracking camera output, onto a pre-operative high-resolution image taken from the preoperative three-dimensional set of images. This implementation thus enables the surgeon to track the position of the surgical tool tip in real time, by means of an image of the tool tip region implanted on a high resolution image, such as a CT or MM image, from which the surgical plan was developed. In the presently described implementation, such an image implantation using the image information generated by both the tool directed camera, and the body part directed camera, can provide a continuous, real-time view of a surgical tool implanted onto a high resolution CT or MM image of the region of interest.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

What is claimed is:

1. A robotic system comprising:
   a first tracking camera fixedly attached to a part of a robot, in a position that enables the first tracking camera to capture images of a first three-dimensional reference frame attached to a surgical tool;
   a second tracking camera fixedly attached to a part of the robot, in a position that enables the second tracking camera to capture images of a second three-dimensional reference frame attached to an anatomical part of a subject; and
   a control system adapted to determine at least a position of the surgical tool in a co-ordinate system, based on images of the first three-dimensional reference frame from the first tracking camera, and to determine a pose of the anatomical part of the subject in the co-ordinate system, based on images of the second three-dimensional reference frame from the second tracking camera, wherein the control system is further adapted to detect in an image of the anatomical part of the subject obtained by at least one of the first and second tracking cameras, an impingement of a laser beam on a predetermined point of the anatomical part of the subject, such that the predetermined point of the anatomical part of the subject illuminated by the laser beam is known in a robot co-ordinate frame.

2. The robotic system according to claim 1, wherein the control system is further adapted to determine an orientation of the surgical tool.

3. The robotic system according to claim 1, wherein the part of the robot is an end effector.

4. The robotic system according to claim 3, wherein the control system is adapted to take into account a position of an operating tip of the surgical tool relative to the position of the surgical tool determined by the first three-dimensional reference frame, such that a longitudinal position of the operating tip of the surgical tool is known relative to the end effector.

5. The robotic system according to claim 4, wherein the anatomical part of the subject is a bone, and the surgical tool is a drill carrying a drill bit adapted to move within a guide sleeve carried by the end effector, and wherein the control system is adapted to track an insertion depth of the drill bit into the bone.

6. The robotic system according to claim 5, wherein the control system is further adapted to use a registration procedure of the co-ordinate system with a set of preoperative three-dimensional images of at least the bone, such that the drill bit is oriented and positioned relative to the bone according to a surgical plan generated from the preoperative three-dimensional set of images.

7. The robotic system according to claim 6, wherein the control system is further adapted to compare the pose of the anatomical part of the subject determined by an image registration procedure with the pose of the anatomical part of the subject determined from the images from the second tracking camera, such that the pose of the anatomical part is intraoperatively verifiable.

8. The robotic system according to claim 1, wherein at least one of the first tracking camera and the second tracking camera enables generation of three-dimensional images.

9. The robotic system according to claim 1, wherein at least one of the first and the second tracking cameras are adapted to be fixedly attached to an end effector in a position no further than 100 centimeters from the first three-dimensional reference frame at which the first tracking camera is directed.

10. The robotic system according to claim 9, wherein at least one of the first and the second tracking cameras are adapted to be fixedly attached to the end effector in a position no further than 50 centimeters from the first three-dimensional reference frame at which the first tracking camera is directed.

11. The robotic system according to claim 10, wherein at least one of the first and the second tracking cameras are adapted to be fixedly attached to the end effector in a position no further than 20 centimeters from the first three-dimensional reference frame at which the first tracking camera is directed.

12. The robotic system according to claim 11, further comprising a third reference frame fixedly attached to a touch probe, such that at least one of the first and second tracking cameras attached to the end effector of the robot can determine the position of the touch probe in the robot co-ordinate frame, enabling points of the anatomical part of the subject touched by the touch probe to be registered in the robot co-ordinate frame.

13. The robotic system according to claim 1, wherein the control system is further adapted to determine a position of a surgical tool tip relative to the anatomical part of the subject, without need of registration with preoperative images of the subject.

14. The robotic system according to claim 1, wherein the surgical tool is hand-held.

15. A robotic system comprising:
   a first imaging camera fixedly attached to a first robotic arm, and directed to generate first two-dimensional images of a three-dimensional reference frame attached to a hand-held surgical tool;
   a second imaging camera fixedly attached to a second robot arm and directed to generate second two-dimensional images of the three-dimensional reference frame attached to the hand-held surgical tool; and
   a control system adapted to determine from a first two-dimensional image from the first imaging camera, and from a second image from the second two-dimensional imaging camera, a three-dimensional pose of the hand-held surgical tool in a coordinate system of at least one of the first and the second robot arms,
   wherein positions of the first and second robotic arms are adapted to be held at a distance apart that provides a desired accuracy of the three-dimensional pose of the hand-held surgical tool, and
   wherein the control system is further adapted to detect in an image of the anatomical part of the subject obtained by at least one of the first and second tracking cameras, an impingement of a laser beam on a predetermined point of the anatomical part of the subject, such that the predetermined point of the anatomical part of the subject illuminated by the laser beam is known in a robot co-ordinate frame.

16. The robotic system according to claim 15, further comprising a third three-dimensional reference frame attached to an anatomical part of a subject on which the hand-held surgical tool is to perform a surgical procedure, such that the first and the second imaging cameras can provide information to enable the three-dimensional pose of the anatomical part of the subject to be determined in the coordinate system of at least one of the first and the second robot arms.

17. The robotic system according to claim 16, wherein the first and second robotic arms are adapted to be held at a distance sufficiently close to the three-dimensional reference frame attached to the anatomical part of the subject, to achieve a desired accuracy of a determined three-dimensional pose of the anatomical part of the subject.

* * * * *